(12) United States Patent
Weir (10) Patent No.: US 6,619,956 B1
(45) Date of Patent: Sep. 16, 2003

(54) DENTAL MATRIX STRIP

(76) Inventor: C. Douglas Weir, RR3 Box 26506, Mitchell, IN (US) 47446

( * ) Notice: Subject to any disclaimer, the term of this patent is extended or adjusted under 35 U.S.C. 154(b) by 0 days.

(21) Appl. No.: 10/146,643

(22) Filed: May 15, 2002

(51) Int. Cl.[7] ................................................. A61C 5/12
(52) U.S. Cl. ........................................ 433/39; 433/149
(58) Field of Search .......................... 433/39, 40, 148, 433/149, 155

(56) References Cited

U.S. PATENT DOCUMENTS

| | | | |
|---|---|---|---|
| 164,870 A | | 6/1875 | Palmer |
| 532,723 A | | 1/1895 | Dennis |
| 677,268 A | | 6/1901 | Power |
| 1,669,231 A | | 5/1928 | Curran |
| 3,108,377 A | * | 10/1963 | Meyer |
| 3,482,314 A | * | 12/1969 | Tofflimiri |
| 3,795,052 A | | 3/1974 | Mowery |
| 3,842,505 A | * | 10/1974 | Eames |
| D253,191 S | | 10/1979 | Stark et al. |
| 4,824,365 A | * | 4/1989 | von Weissenfluh ........... 433/40 |
| 5,342,194 A | | 8/1994 | Feldman ...................... 433/39 |
| 5,425,635 A | | 6/1995 | Croll ........................... 433/39 |
| 5,620,322 A | | 4/1997 | Lococo ........................ 433/39 |
| 5,730,592 A | | 3/1998 | Meyer .......................... 433/39 |
| 5,788,487 A | | 8/1998 | Meyer .......................... 433/39 |
| 6,007,334 A | | 12/1999 | Suhonen ....................... 433/39 |
| 6,142,778 A | * | 11/2000 | Summer ....................... 433/39 |
| 6,234,793 B1 | | 5/2001 | Brattesani et al. ............ 433/39 |
| 6,293,796 B1 | | 9/2001 | Trom et al. .................. 433/155 |
| 6,325,625 B1 | | 12/2001 | Meyer ......................... 433/139 |
| 6,350,122 B1 | * | 2/2002 | Meyer ........................... 433/39 |
| 6,482,005 B1 | * | 11/2002 | Summer et al. .............. 433/39 |

OTHER PUBLICATIONS

StopStrip dental product package from Premier Dental Products Company and printed photo image of product, No date.

* cited by examiner

Primary Examiner—Ralph A. Lewis
(74) Attorney, Agent, or Firm—Kyle S. Brant

(57) ABSTRACT

An elongated flexible dental matrix strip is disclosed. The strip includes a raised portion extending outward from the surface of the strip. The raised portion tapers towards the distal end of the strip in one embodiment and tapers toward both ends of the strip in another embodiment. The raised portion is sized so that when the strip is inserted between adjacent teeth an interference fit occurs. A light force is used to slide the strip into position between adjacent teeth in such a fashion as to anchor the strip in position. The strip serves to contain filling material in a tooth cavity while the filling material or resin hardens. Another embodiment includes a curved surface along one edge of the strip wherein the raised tapered portion is disposed. Yet another embodiment includes two raised tapered portions in parallel with one another.

25 Claims, 5 Drawing Sheets

DENTAL MATRIX STRIP

FIELD OF THE INVENTION

The present invention relates in general to devices used in the field of dentistry, and more particularly, to a dental matrix strip.

BACKGROUND OF THE INVENTION

A dental matrix is typically used by dentists to retain packed filling material in position within a tooth prepared cavity. Such devices have been in use for a considerable time.

Prior art examples of various dental matrix, shim and clamping devices are shown in U.S. Pat. Nos. 5,620,322 (Lococo), 3,795,052 (Mowery), 5,788,587 (Meyer), 6,007,334 (Suhonen), 6,234,793 (Brattesani et al.), 5,730,592 (Meyer), 677,268 (Power), 532,723 (Dennis), 164,870 (Palmer), 1,669,231 (Curran), 5,425,635 (Croll), 5,342,194 (Feldman), 6,293,796 (Trom et al.), and 6,325,625 (Meyer). Various matrix devices fashioned from thin sheet-like material are shown in these patents. Several of the devices are intended for use with bicuspid and molar teeth.

One of the difficulties encountered by dentists when filling an interproximal cavity (a cavity that develops on the side of a tooth) is in securing the filling material within the cavity during the curing time for the filling material. Typically, a dental matrix device is used to retain filling material within the cavity while the filling material hardens or is cured. If the matrix is not securely stabilized, the matrix can be inadvertently moved by the patient or dentist during the procedure. Any movement of the matrix from its interproximal position is likely to allow the filling material to flow outside the cavity preparation, or create a void in the filling material.

Typical matrix bands of the prior art used by dentists are thin elongated plastic strips (oftentimes made from Mylar® or polyester film) having a thickness ranging from less than 0.001" to 0.030". The known prior art dental matrix devices have failed to provide a reliable mechanism for securing the matrix in an interproximal position, without the separate use of wedge devices. Due to the variations in the interproximal anatomy, conventional wedge devices often will not fit between the teeth properly.

What is needed is a dental matrix device that includes a design for readily inserting the device in an interproximal position and a mechanism for securing the device in position between adjacent teeth to retain filling material within a cavity during the curing process and to prevent inadvertent movement of the matrix. A dental matrix that includes such a position securing mechanism and that accommodates a wide range of interproximal spacing is needed.

SUMMARY OF THE INVENTION

A dental matrix strip, according to one aspect of the present invention, comprises an elongated flexible strip having a front surface, a rear surface, an upper edge, a lower edge, a first end and a second end, and the strip includes an elongated tapered portion disposed on the front surface of the strip and extending outward from the front surface of the strip, the tapered portion situated near and along the upper edge of the strip and having a larger height above the strip substantially near the center of the strip and diminishing to nominal thickness near the first end of the strip.

One object of the present invention is to provide an improved dental matrix device.

Another object of the present invention is to provide a dental matrix having an anchoring feature to secure the matrix in position between teeth, without the need for a separate wedge device.

Yet another object of the present invention is to provide an inexpensive dental matrix device.

Still another object is to provide a dental matrix that is universally applicable to any of a variety of inter-dental tooth spacing, and anatomy.

These and other objects of the present invention will become more apparent from the following figures and description of the preferred embodiment.

DESCRIPTION OF THE PREFERRED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 1:
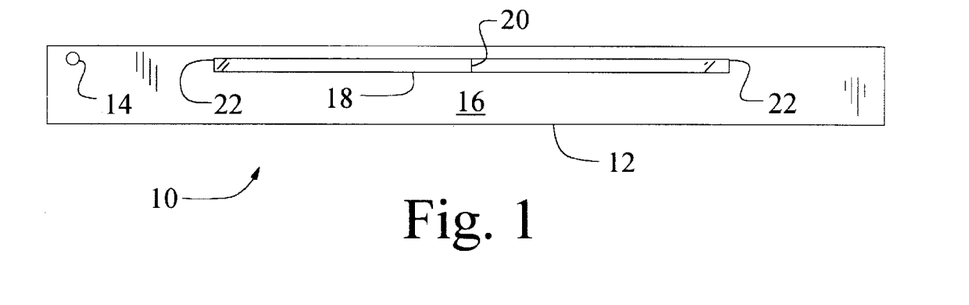
FIG. 1 is a front elevational view of a dental matrix strip according to one aspect of the present invention.

Referring now to FIG. 1, a dental matrix strip 10 according to one aspect of the present invention is shown. The matrix strip (or matrix) 10 includes an elongated resilient and flexible thin strip 12 that is substantially rectangular in shape. An aperture 14 is provided to receive a dental tool and aid in insertion of the matrix 10 between the teeth of a patient. Extending outward from front surface 16 of matrix 10 is a raised portion or tapered portion 18. Tapered portion 18 has a maximum thickness or height at location 20. At locations 22 tapered portion 18 decreases in height to zero thickness. Tapered portion 18 provides a mechanism for fixedly positioning matrix 10 in an interproximal position between two anterior teeth. Further, tapered portion 18, as is discussed below in association with FIGS. 20 and 21, urges matrix 10 against the area in which a cavity has been filled with packing or filling material so that air bubbles are forced out of the filling material, as well as serving to retain the filling material within the cavity preparation of the tooth during the time required for the filling material to be polymerized, or to set.

Matrix 10 is fabricated from any of various well known materials, preferably plastics, such as Mylar® polyester film, Nylon® or other suitable and similar resilient and flexible plastics. Preferably, matrix 10 is fabricated from transparent or translucent plastics since modern cavity filling compounds are cured or hardened via exposure to specific wavelengths of light. Other suitable materials contemplated include rubber-like compounds. Preferably a plastic molding process is used to manufacture matrix 10 or cut from sheet stock. It is contemplated that any flexible and perhaps resilient material that is considered safe for use in an oral cavity of a dental patient may be used in the fabrication of matrix 10. It should be noted that the thickness of matrix 10 is exaggerated in the figures for ease in illustrating the features of the device and that a relatively thin strip 12 (0.0005 inches to 0.050 inches) is contemplated.

Figure 2:
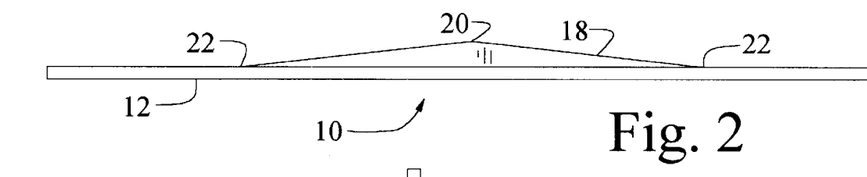
FIG. 2 is a bottom view of the matrix strip shown in FIG. 2.

Referring now to FIG. 2, a bottom view of matrix 10 is shown. From this view it is readily seen that tapered portion 18, extending outward from strip 12, has a maximum height at location 20 and tapers to zero thickness at locations 22. Tapered portion 18 is integrally formed with strip 12 during manufacturing of matrix 10 and such a configuration is believed the most economical technique for producing matrix 10. It is conceivable that tapered portion 18 and strip 12 may be manufactured as separate components and attached to one another using an ultrasonic welding process, adhesives or other well known manufacturing processes for joining plastic components into a single unitary assembly. A resilient substance such as silicone glue (preferably clear) is also contemplated for fabricating the raised tapered portion 18. Alternatively, the raised portion may be an elongated bead of silicone glue having a taper only at the ends of the bead of glue. Resiliency in the tapered portion 18 provides increased gripping capability with the tooth in contact therewith as well as providing a matrix that is usable over a wider range of tooth spacing. Some or all surfaces of the matrix 10 optionally may include a rough texture to increase frictional forces between matrix 10 and the teeth in contact therewith.

Figure 3:
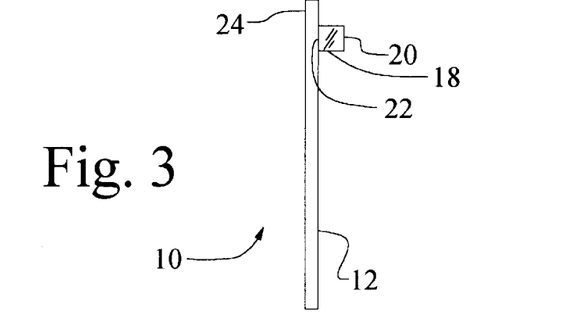
FIG. 3 is an end view of the matrix strip shown in FIG. 1.

Referring now to FIG. 3, an end view of matrix 10 is shown. From this perspective it is seen that tapered portion 18 extends above the surface of strip 12 to a maximum height at location 20 and has a minimal height or taper at location 22. In view of the variations in spacing that are found with various dental patients, the height of tapered portion 18 can vary due to the wide variety of interproximal tooth spacing found in different patients. The height of tapered portion 18 can be increased to any dimension sufficient so that the thickness of strip 12 and tapered portion 18 is greater than interproximal tooth spacing. However, it may be uncomfortable and impractical to use a matrix 10 with a larger height tapered portion with a patient having a small mouth (such as a child) and fairly small interproximal tooth spacing. Thus, it is contemplated that the invention be manufactured in a variety of dimensional sizes.

Dentists find cavities located near the gum line to be difficult at times to fill due to the filling material oozing out of the cavity preparation using dental matrixes of the prior art. With the present invention, the matrix 10 includes a small area 24 of strip 12 that extends below the gum line and serves, in conjunction with tapered portion 18, to retain filling material within the cavity. Further discussion of this aspect of the invention is set forth below.

Figure 4:
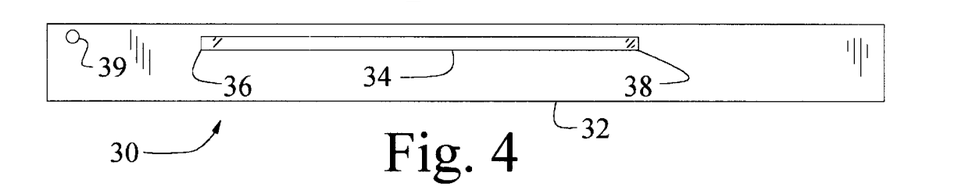
FIG. 4 is a front elevational view of another dental matrix strip according to the present invention.
Figure 5:
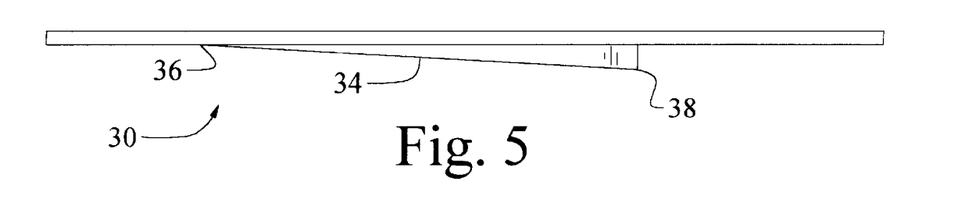
FIG. 5 is a bottom view of the matrix strip shown in FIG. 4.

Referring now to FIGS. 4 and 5, another embodiment of a dental matrix strip 30 according to the present invention is shown. In this embodiment a rectangular cross-section tapered portion 34 extends outward from the surface of strip 32 with a minimal height at location 36 and a maximum height at location 38. Tapered portion 34 serves to urge strip 32 in contact with a tooth when matrix 30 is inserted longitudinally between adjacent teeth. Tapered portion 34 may be situated above or below the interproximal contact point, depending upon the location of a cavity in a tooth. If the cavity is nearer the gum line, matrix 30 is oriented for insertion between adjacent teeth so that tapered portion 34 is situated near the gum line. Alternatively, if the cavity is near the top of a tooth, matrix 30 should be oriented for insertion between the teeth with tapered portion 34 near the top of the teeth. Aperture 39 receives a dental explorer or similar instrument to aid in installation of matrix 30 in between adjacent teeth.

Matrix 30 provides a taper in a single direction and thus is unidirectional to insert in an interproximal position in comparison with matrix 10 which is omnidirectional in usage. However, regarding functionality, the same wedging or locking in position functionality is achieved with either matrix 10 or 30. Further, matrix 30 provides the same feature of urging strip 32 towards a tooth (having a cavity) to retain filling material in position within the cavity of the tooth. Matrix 30 may be used where a wider variance in interproximal spacing exists since tapered portion 34 may have a larger variance in height versus matrix 10, Referring now to FIG. 6, another embodiment of a dental matrix strip 40 according to the present invention is shown.

Figure 6:
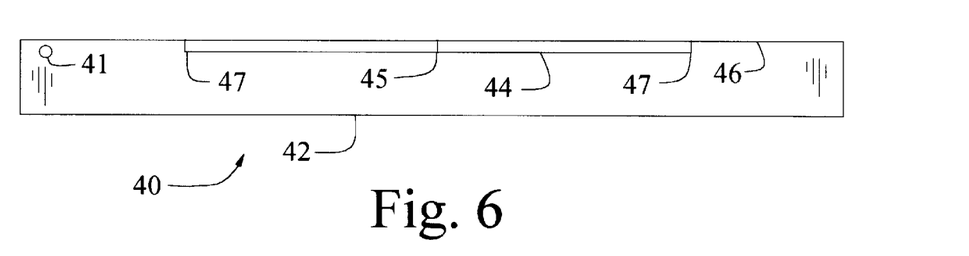
FIG. 6 is a front elevational view of another embodiment of a dental matrix strip according to the present invention.

In this embodiment, the wedge shaped tapered portion 44 that extends above the surface of strip 42 is disposed immediately along the edge 46 of strip 42 and has maximum height at location 45 and a minimum height at location 47. It is contemplated that circumstances can arise wherein the anchoring or locking feature of tapered portion 44 is desirable at the outermost edge 46 of strip 42 and this embodiment reflects the details of such an embodiment. The cross-sectional geometry of tapered portion 44 may be of any geometric shape, and the rectangular shape shown is merely illustrative of one such configuration. Also shown is aperture 41 which is intended to receive a dental tool to aid in pulling and positioning matrix strip 40 between adjacent teeth.

Referring now to FIGS. 7–11, a series of end views of dental matrix strips according to the present invention are shown including a variety of cross-sectional configurations for the tapered portion or anchor portion of the present invention. Each of the embodiments of FIGS. 7–11 may include a single directional taper such as is shown in FIG. 4 or a dual directional taper as is shown in FIG. 1. Of primary significance is the multitude of cross-sectional configurations for the tapered portion of each matrix strip that may be useful given the variety of patient tooth configurations found in practice.

Figure 7:
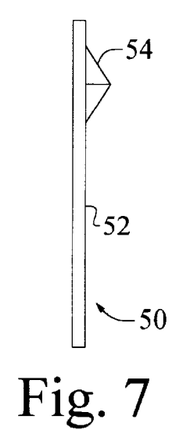
FIG. 7 is an end view of a dental matrix strip including a triangular tapered portion.

FIG. 7 depicts an end view of a dental matrix strip 50 having a raised tapered portion 54 that is triangular in cross-section and extends outward from the surface of elongated flexible strip 52. Tapered portion 50 may taper in a unidirectional fashion, or bidirectionally from a central location of strip 52 outward to the distal ends of strip 52.

Figure 8:
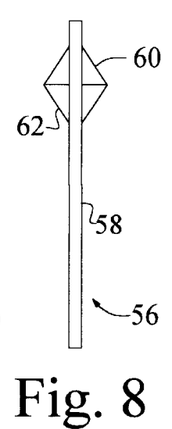
FIG. 8 is an end view of a dental matrix strip having a tapered portion extending outward from both surfaces of the strip.

FIG. 8 shows an end view of a dental matrix strip 56 that includes an elongated flexible strip 58 and a first tapered portion 60 and a second tapered portion 62 extending outward on opposite sides of strip 58. The tapered portions 60 and 62 have a triangular cross-section in this embodiment, though any conceivable geometric cross-section may be used for the tapered portions 60 and 62 in this configuration of the present invention.

Figure 9:
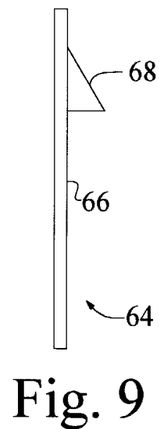
FIG. 9 is an end view of a dental matrix strip having a right triangular tapered portion on one surface of the strip.

FIG. 9 depicts another configuration of the matrix strip 64 according to the present invention. This embodiment has a flexible strip 66 and a tapered portion or member 68 that has a right-triangular cross-sectional configuration.

Figure 10:
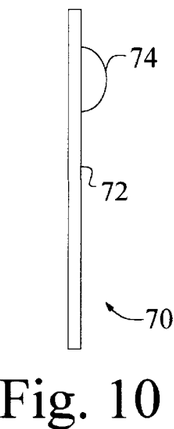
FIG. 10 is an end view of a dental matrix strip having a semicircular tapered portion.

Referring now to FIG. 10, a dental matrix strip 70 according to another aspect of the present invention is shown. Matrix 70 is comprised of an elongated flexible strip 72 and a raised tapered portion 74 that extends above the surface of elongated flexible strip 72. Tapered portion 74 has a semi-circular or semi-elliptical cross-sectional configuration.

Figure 11:
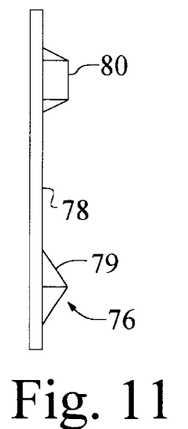
FIG. 11 is an end view of a dental matrix strip having a trapezoidal tapered portion.

Referring now to FIG. 11, another configuration of the dental matrix strip 76 according to the present invention is shown. Matrix 76 includes an elongated flexible strip 78 and a tapered portion 80 extending above strip 78 that is trapezoidal in cross-section.

Figure 12:
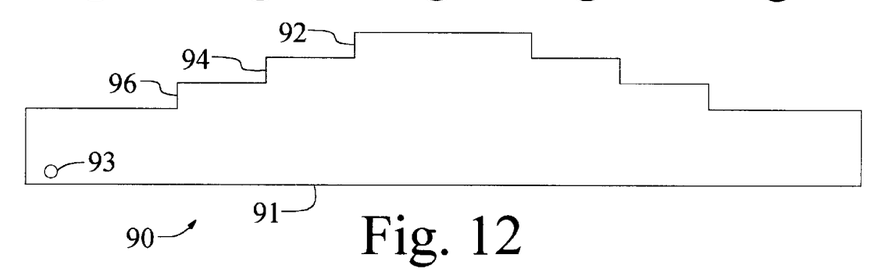
FIG. 12 is a front elevational view of another embodiment of a dental matrix strip according to the present invention.
Figure 13:
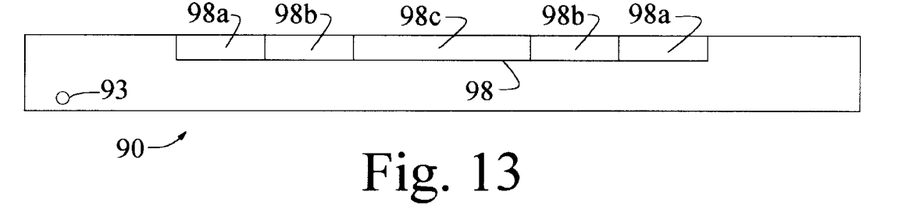
FIG. 13 is a front elevational view of the matrix strip of FIG. 12 showing the flaps folded over the strip to create raised anchor portions.

Referring now to FIGS. 12 and 13, a dental matrix strip 90 according to another aspect of the present invention is shown. Matrix 90 is stamped or cut from a sheet 91 of thin flexible material as shown in FIG. 12. Aperture 93 is intended to receive a dental tool to aid in positioning matrix 90 between adjacent teeth. Rectangular portions 92, 94 and 96 are repeatedly folded over one another in stepped fashion and fixedly attached to each other and to the underlying sheet 91 to form a device that has a raised portion 98 (that serves to lock or anchor the device between teeth) as shown in FIG. 13. The thickness of the raised portion 98 has a first thickness at 98a, a larger height or thickness at 98b and is thickest at location 98c. Manufacturing processes well known in the art of plastics are contemplated for producing the matrix strip 90. Ultrasonic welding techniques or adhesives are suitable for attaching the folded over stepped portions 92, 94 and 96 to each other and to flexible sheet 91.

Figure 14:
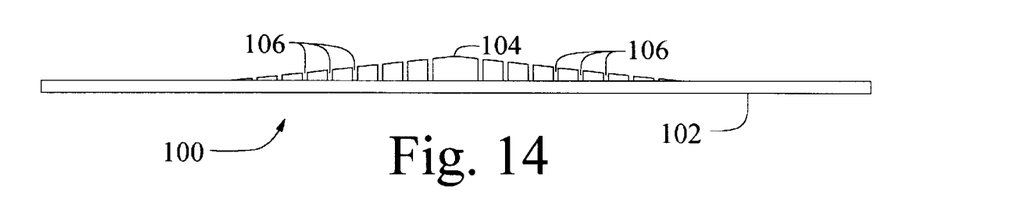
FIG. 14 is a top view of the dental matrix strip of FIG. 1 and including serrations.

Referring now to FIG. 14, a bottom view of a dental matrix strip 100 according to another aspect of the present invention is shown. Strip 100 includes an elongated flexible strip 102 and a raised tapered portion 104 extending above strip 102 that includes a plurality of serrations 106. Serrations 106 serve to increase the flexibility of matrix strip 100 yet enable a larger height dimension for tapered portion 104. Any of the various configurations shown in FIGS. 1–11 may include the serrations shown in FIG. 14 to improve the usability of a matrix strip according to the present invention.

Figures 15, 16, 17, 18:
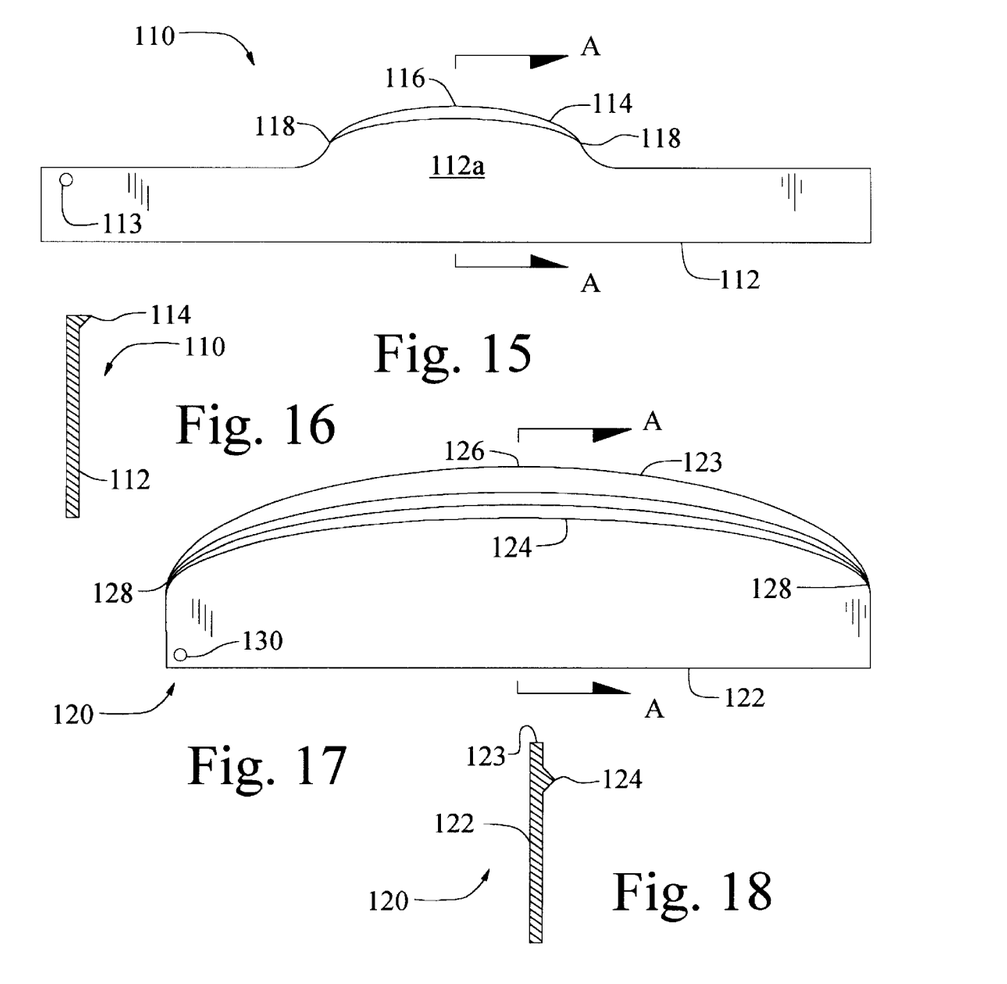
FIG. 15 is another embodiment of a dental matrix strip according to the present invention.
FIG. 16 is a cross-sectional view of the matrix of FIG. 15 looking in the direction of the arrows labeled A—A.
FIG. 17 is another embodiment of a dental matrix strip according to the present invention.
FIG. 18 is a cross-sectional view of the matrix strip of FIG. 17 looking in the direction of the arrows labeled A—A.

Referring now to FIGS. 15 and 16, another embodiment of a dental matrix strip 110 according to the present invention is shown. Matrix 110 is comprised of an elongated thin flexible strip 112 and a tapered member or tapered raised portion 114 that extends outward from surface 112a of strip 112. Strip 112 has an arcuate or semi-elliptical contour at its upper edge between locations 118 and location 116. Similarly, tapered member 114 follows a semi-elliptical path along the upper edge of strip 112 between locations 118 and location 116. Also shown is an aperture 113 for receiving a dental pick to aid the dentist in positioning matrix strip 110 in an interproximal position. Tapered member 114 has a maximum thickness in the vicinity of location 116 and a minimal profile height or thickness at locations 118. Matrix strip 110 has a triangular raised tapered portion 114, however, any of the prior geometric configurations discussed in regard to other embodiments set forth herein are contemplated for the cross-section of tapered portion 114.

FIG. 16 is a cross-sectional view of strip 110, looking in the direction of the arrows labeled A—A in FIG. 15. FIG. 15 provides additional detail of tapered portion 114 extending outward from the surface of flexible strip 112. Tapered portion 114 is situated at the upper edge of strip 112 but is optionally positionable a predetermined distance offset from the edge of strip 112 at locations 116 and 118 and continuously therebetween.

Referring now to FIGS. 17–18, another embodiment of a dental matrix strip 120 according to the present invention is shown. FIG. 18 is a cross-sectional view looking in the direction of the arrows A—A of FIG. 17. Strip 122 is made from a thin flexible material and has an arcuate or semi-elliptical edge 123. A raised tapered portion 124 is shown spaced apart from edge 123 and situated along a semi-elliptical line extending along edge 123 in near proximity thereto. As in the previous embodiments, the tapered portion 124 has a maximum height in the vicinity of location 126 and a minimum height or nominal height at locations 128. Also shown is aperture 130 for receiving a dental instrument and facilitating the positioning of matrix strip 120 between adjacent teeth. Aperture 130, in this and all other embodiments disclosed, may include surrounding reinforcement to avoid tearing the matrix when forces are applied thereto. A metal grommet, silicone glue or additional plastic material around the aperture provides such reinforcement.

The embodiments shown in FIGS. 14–17 are intended for applications wherein a cavity is located near the gum line. The arcuate edges make usage of the devices slightly easier to position between a patient's teeth since the matrixes are rotated slightly and pulled into position rather than pulled in a linear fashion into position between adjacent teeth.

Figures 19, 20:
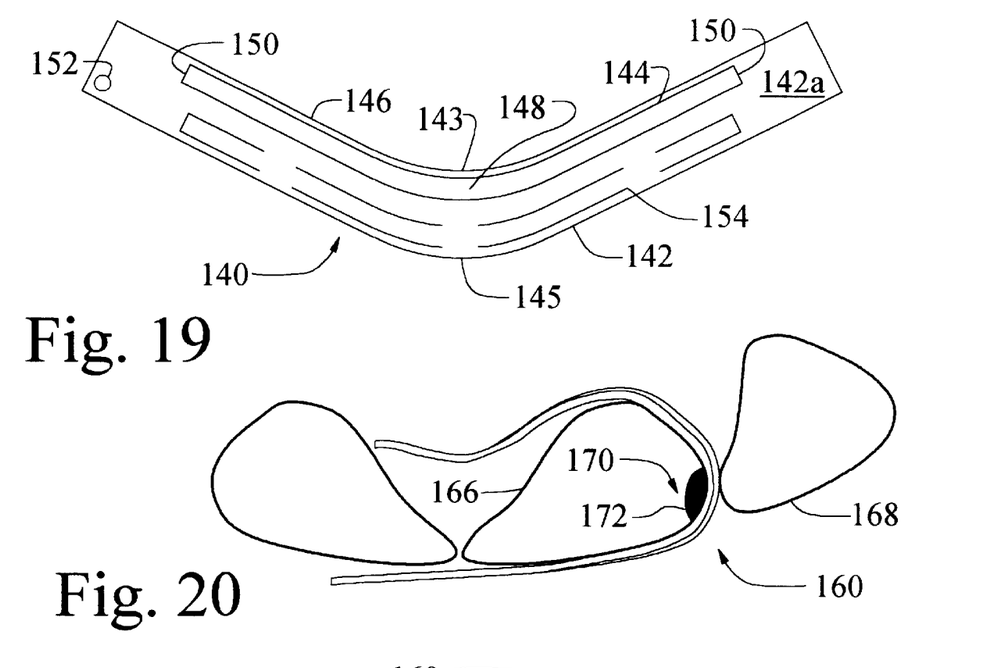
FIG. 19 is a front elevational view of another embodiment of a dental matrix strip according to the present invention.
FIG. 20 is a partial plan view of a patient's mouth depicting a dental matrix strip according to the present invention situated in normal usage position.

Referring now to FIG. 19, another embodiment of a dental matrix strip 140 according to the present invention is shown.

Matrix 140 includes a non-linear elongated strip 142 having an arcuate bend or curved portion at locations 143 and 145. A raised tapered portion 144 is shown disposed along and spaced apart from edge 146 (though it is contemplated tapered portion 144 can be immediately adjacent edge 146). Tapered portion 144 has a maximum height above surface 142a at location 148 and a minimal height at locations 150. In this embodiment, tapered portion 144 is rectangular in cross-section, but can be similar in configuration to any of the raised tapered portions discussed above in regard to the various embodiments of the invention. An aperture 152 is provided to aid in installation and usage of matrix strip 140. Optionally, raised tapered portion 144 can be positioned adjacent location 145 as shown by broken lines at 154.

It should be apparent from the variety of configurations shown in FIGS. 1–19 that there are a multitude of variations for the present invention that all include certain basic features, namely, an elongated flexible strip and an elongated raised tapered portion situated near and along one of the elongated edges of the strip and wherein the raised portion includes a profile height taper that is unidirectional or bi-directional in configuration. It is also contemplated that any of the embodiments shown may include multiple raised tapered portions that extend along both of the elongated edges of a thin elongated flexible strip. Combinations of different geometrical cross-sectional configurations (such as triangular, square, trapezoidal, semi-elliptical etc.) can be implemented in a matrix strip having more than one raised tapered portion or member.

Figure 21:
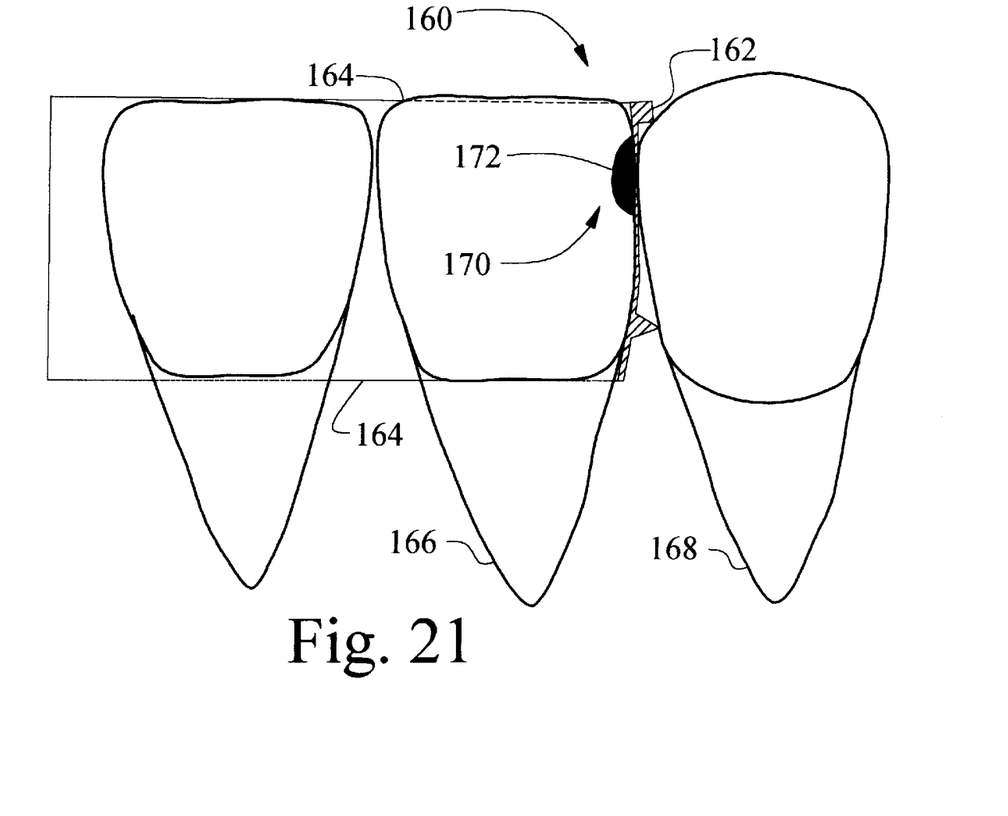
FIG. 21 is a partial elevational view of a patient's teeth depicting a partial cross-sectional view of a dental matrix strip situated in one usage position.

Referring now to FIGS. 20 and 21, a plan view and a cross-sectional front elevational view of a dental matrix strip 160 situated in an interproximal position are shown. Matrix 160 (identical in features to matrix strip 40 of FIG. 6) has a rectangular tapered portion 162 extending outward from the flexible strip 164. Matrix 160 is positioned between two adjacent teeth 166 and 168. Then, a dentist fills cavity 170 with a filling material 172. Next, the dentist pulls the ends of the matrix around the teeth to force bubbles out of the filling material and pack the filling material into the cavity. Matrix 160 is urged toward tooth 166 by forces between tapered portion 162 and tooth 168. Tapered portion 166 acts as a cam mechanism to urge matrix strip 160 in a desired direction. Further, tapered portion 162, when wedged in position between teeth 166 and 168, acts as a locking mechanism to secure matrix strip 160 firmly in position as shown. Filling material 172 is contained within cavity 170 as a result of the forces applied to strip 164 by tapered portion 162 urging strip 164 against tooth 166. Any inadvertent contact with the matrix by the dentist or the patient is unlikely to cause the matrix to slip or dislodge from its fixed position.

Figure 22:
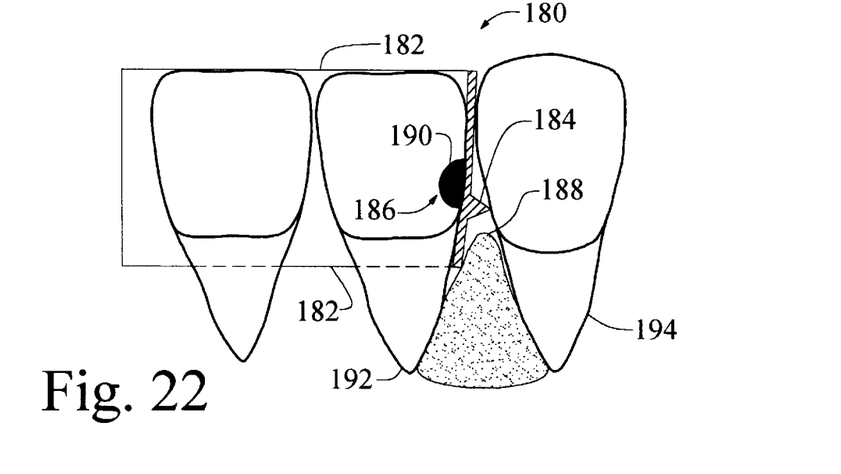
FIG. 22 is a partial elevational view of a patient's teeth depicting a partial cross-sectional view of a dental matrix strip disposed in an interproximal position application wherein a cavity is located near the gum line.

Referring now to FIG. 22, a front elevational cross-sectional view of a dental matrix strip 180 disposed in position within a patient's mouth is shown. Matrix 180 is similar in features to matrix 50 shown in FIG. 7. In this example application of the present invention, a cavity 186 is located near the gum line 188. Matrix strip 180 is situated as shown between teeth 192 and 194 and filling material 190 is then deposited into cavity 186 by a dentist. Flexible strip 182 includes a tapered portion 184, that is triangular in cross-section, and extends outward from strip 182. Tapered portion 184 urges strip 182 into contact with tooth 192 and prevents filling material 190 from escaping cavity preparation 186. Further, the gradual taper of tapered portion 184 urges strip 182 against tooth 192 so that frictional forces maintain the matrix strip 180 in position while the filler material hardens.

Gum line cavities make cavity filling difficult, and the problem of preventing filling material from escaping the cavity is resolved by tapered portion 184 having an offset location from the edge of strip 182 so that a portion of strip 182 can be situated below the gum line. A longitudinal force is applied to strip 182 by tapered portion 184 at the gum line to maintain cavity filling material 190 within cavity 186. In the past, if filling material oozed out of the cavity near the gum line, a dentist would be forced to remove the excess with great difficulty. With the present invention, the necessity of grinding or shaping the filling material is minimized.

Figure 23:
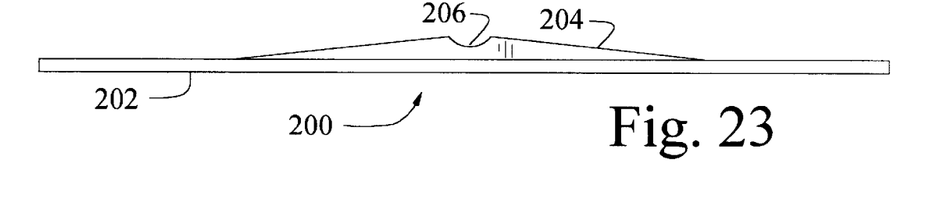
FIG. 23 is a front elevational view of another dental matrix strip according to the present invention.

Referring now to FIG. 23, another embodiment of a matrix strip 200 according to the present invention is shown. Matrix 200 is identical in all aspects with matrix 10 of FIG. 1 with the exception of semi-cylindrical indentation or notch 206. In application, matrix 200 is positioned between the teeth with notch 206 disposed at the interproximal contact point. Notch 206 enhances the functionality of tapered portion 204 in preventing matrix 200 from being moved or dislodged once placed in position between the teeth. Notch 206 may optionally be configured with planar surfaces to form a v-type notch. Any of the embodiments shown herein may be modified to include a notch 206 as shown in FIG. 23.

Figures 24, 25:
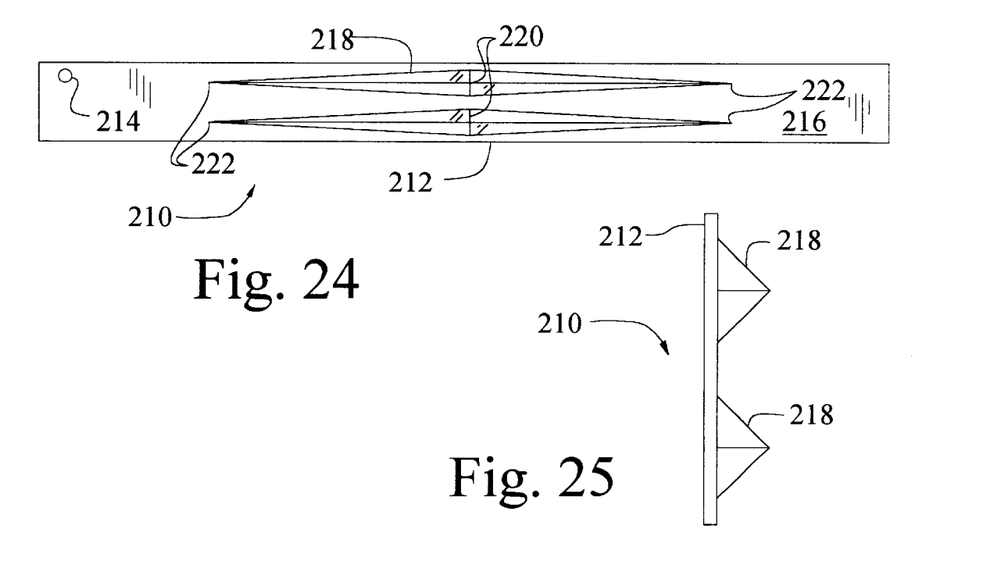
FIG. 24 is a plan view of another dental matrix strip according to the present invention.
FIG. 25 is an end view of the matrix shown in FIG. 24.

Referring now to FIGS. 24 and 25, yet another embodiment of a dental matrix strip 210 according to the present invention is shown. Matrix 210 includes an elongated flexible strip 212 having two raised tapered portions 218 extending outward from surface 216. Tapered portions 218 have a maximum height at location 220 and a minimum height at location 222. Further, tapered portions 218 taper in width to a minimum width at location 222, as well as height. In use, matrix 210 is longitudinally inserted between adjacent teeth so that the interproximal contact point is located between raised tapered portions 218. Also shown is an aperture. 214 for receiving a dental instrument to aid in installing matrix 210. Clear plastic or polyester film is preferred as the material used in fabricating matrix 210.

While the invention has been illustrated and described in detail in the drawings and foregoing description of the preferred embodiments, the same is to be considered as illustrative and not restrictive in character, it being understood that only the preferred embodiments have been shown and described and that all changes and modifications that come within the spirit of the invention are desired to be protected.

What is claimed is:

1. A dental matrix strip comprising:
   an elongated flexible strip having a front surface, a rear surface, an upper edge, a lower edge, a first end and a second end; and
   said strip including an elongated tapered portion disposed on said front surface of said strip and extending outward from said front surface of said strip, said tapered portion situated near and along said upper edge of said strip and having a larger height above said strip substantially near the center of said strip and diminishing to nominal thickness near said first end of said strip.

2. The dental matrix strip of claim 1 wherein said tapered portion extends towards said distal end and said proximal end of said strip, and wherein said tapered portion is thickest at a location substantially central between said first and said second ends of said strip and diminishes to nominal thickness near said first end and near said second end of said strip.

3. The dental matrix strip of claim 2 wherein said tapered portion has a triangular cross-section.

4. The dental matrix strip of claim 2 where said tapered portion has a rectangular cross-section.

5. The dental matrix strip of claim 2 where said tapered portion has a semi-circular cross-section.

6. The dental matrix strip of claim 2 where said tapered portion has a semi-elliptical cross-section.

7. The dental matrix strip of claim 2 wherein said tapered portion includes a plurality of transverse slots formed therein.

8. The dental matrix strip of claim 2 wherein the length of said strip from said proximal end to said distal end is larger than the diameter of a tooth.

9. A dental matrix strip comprising:

an elongated flexible strip having a front surface, a rear surface, an upper edge, a lower edge, a proximal end and a distal end; and anchor means disposed on said front surface of said strip in near proximity to and along said upper edge of said strip, said anchor means providing an increased thickness to said flexible strip to fixedly wedge said strip between adjacent teeth.

10. The dental matrix strip of claim 9 wherein said upper edge of said strip includes a portion that is semi-elliptical and said anchor means is situated along said semi-elliptical portion of said upper edge.

11. The dental matrix of claim 9 wherein said elongated strip is rectangular in shape.

12. The dental matrix of claim 9 wherein said anchor means has a thicker dimension near the center of said elongated strip and diminishes in thickness towards said proximal end of said strip.

13. The dental matrix of claim 12 where said anchor means diminishes in thickness towards said distal end of said strip.

14. The dental matrix of claim 12 wherein said anchor means has a geometric cross-section with at least three sides.

15. The dental matrix of claim 12 wherein said anchor means has a semi-elliptical cross-section.

16. A dental matrix strip comprising:

an elongated resilient flexible strip having a lower edge, an upper edge, a first end and a second end;

an elongated flexible member attached to said flexible strip, said elongated member attached to said strip near said lower edge of said strip, said elongated flexible member extending outward from said strip to a height that diminishes near said first end of said strip and increases in height towards said second end of said strip, said elongated flexible member having a width less than half the distance from said lower edge to said upper edge of said flexible strip.

17. The device of claim 16 wherein said elongated flexible member is integrally formed as a part of said elongated resilient flexible strip.

18. A dental matrix strip comprising:

an elongated resilient flexible strip having a lower edge, an upper edge, a first end and a second end;

an elongated flexible member attached to said flexible strip, said elongated member attached to said strip near said lower edge of said strip, said elongated flexible member extending outward from said strip to a height that diminishes near said first end and said second ends of said strip and is of maximum height near the midpoint between said first and second ends of said strip, said elongated flexible member having a width less than half the distance from said lower edge to said upper edge of said flexible strip.

19. The device of claim 18 said elongated flexible member is integrally formed as a part of said elongated resilient flexible strip.

20. The device of claim 19 wherein said elongated flexible member has a geometric cross-section comprised of at least 3 sides.

21. The device of claim 19 where said elongated flexible member has a geometric cross-section that is semi-elliptical.

22. The device of claim 18 wherein said lower edge of said strip is substantially arcuate and said flexible member is disposed along and near said substantially arcuate lower edge of said strip.

23. The device of claim 18 where said flexible member includes a plurality of serrations.

24. The device of claim 18 wherein said elongated flexible member includes a depression disposed substantially at the midpoint thereof.

25. A dental matrix strip comprising:

an elongated flexible strip having an elongated lower edge, an elongated upper edge, a first end and a second end;

a first elongated flexible member attached to said flexible strip, said first elongated member attached to said strip substantially parallel with and near said lower edge of said strip, said first elongated flexible member extending outward from said strip to a height that diminishes near said first end and said second ends of said strip and is of maximum height near the midpoint between said first and second ends of said strip, said first elongated flexible member having a width less than half the distance from said lower edge to said upper edge of said flexible strip; and a second elongated flexible member attached to said flexible strip, said second elongated member attached to said strip substantially parallel with and near said upper edge of said strip, said second elongated flexible member extending outward from said strip to a height that diminishes near said first end and said second ends of said strip and is of maximum height near the midpoint between said first and second ends of said strip, said second elongated flexible member having a width less than half the distance from said lower edge to said upper edge of said flexible strip.

* * * * *